US011040059B2

(12) United States Patent
Recke et al.

(10) Patent No.: US 11,040,059 B2
(45) Date of Patent: Jun. 22, 2021

(54) TREATMENT OR PREVENTION OF ANAEMIA IN PREGNANT NON-HUMAN MAMMALS

(71) Applicant: Pharmacosmos Holding A/S, Holbæk (DK)

(72) Inventors: Christian von der Recke, Lynge (DK); Tobias S. Christensen, Copenhagen S (DK); Hans Andreasen, Holbaek (DK); Lars Lykke Thomsen, Holte (DK)

(73) Assignee: Pharmacosmos Holding A/S, Holbæk (DK)

( * ) Notice: Subject to any disclaimer, the term of this patent is extended or adjusted under 35 U.S.C. 154(b) by 240 days.

(21) Appl. No.: 15/522,466

(22) PCT Filed: Oct. 27, 2015

(86) PCT No.: PCT/DK2015/050328
§ 371 (c)(1),
(2) Date: Apr. 27, 2017

(87) PCT Pub. No.: WO2016/066172
PCT Pub. Date: May 6, 2016

(65) Prior Publication Data
US 2017/0333470 A1    Nov. 23, 2017

(30) Foreign Application Priority Data

Oct. 27, 2014  (DK) .......................... PA 2014 70654

(51) Int. Cl.
| *A61K 31/721* | (2006.01) |
| *A61K 47/10* | (2017.01) |
| *A61K 9/00* | (2006.01) |
| *A61K 31/295* | (2006.01) |

(52) U.S. Cl.
CPC .......... *A61K 31/721* (2013.01); *A61K 9/0019* (2013.01); *A61K 31/295* (2013.01); *A61K 47/10* (2013.01)

(58) Field of Classification Search
CPC .... A61K 31/295; A61K 31/721; A61K 47/10; A61K 9/0019; A61K 2300/00
USPC .......................................................... 514/59
See application file for complete search history.

(56) References Cited

U.S. PATENT DOCUMENTS

| 3,105,791 | A |  | 10/1963 | Banford et al. |
| 3,259,500 | A | * | 7/1966 | Barnhart ............... A61K 31/295 424/601 |
| 4,076,803 | A |  | 2/1978 | Ashmead |
| 6,291,440 | B1 |  | 9/2001 | Andreasen et al. |

FOREIGN PATENT DOCUMENTS

| CN | 1293577 A |   | 5/2001 |           |
| DE | 102007054794 |   | 5/2009 |           |
| RU | 2274003 |   | 4/2006 |           |
| WO | WO 99/48533 | * | 9/1999 | ............. A61K 47/48 |
| WO | 2012/110489 |   | 8/2012 |           |

OTHER PUBLICATIONS

Leclillet et al, Ann. Zootech., 1968, 17(1), 59-70, English Translation, pp. 1-22.*
Jensen et al , Joint Meeting of the 5th European Symposium of Porcine Health Management, UK 2013 p. 92.*
International Search Report dated Nov. 30, 2015 issued in corresponding International Application No. PCT/DK2015/050328.
Archibald, R.M. and E. Errol I. Hancock. "Iron Deficiency as the Probable Cause of Stillbirth in Swine." *Canadian Journal of Comparative Medicine* 3 (1939): 134.
Auvigne, Vincent et al. "Anaemia in the hyperprolific sow: Effect of injectable iron administration and relation with fattening score." Proceedings of the 21st IPVS Congress, Vancouver (2010).
Bille, N. et al. "Preweaning Mortality in Pigs: 2. The Perinatal Period." *Nordisk Veterinaermedicin* 26 (1974): 294-313.
Egeli A.K. et al. "The Effect of Peroral Administration of Amino Acid-Chelated Iron to Pregnant Sows in Preventing Sow and Piglet Anaemia." *Acta Vet. Scandinav.* 39.1 (1998): 77-87.
Jensen, Anna Kathrine and Jens Peter Nielsen. "Association Between Blood Haemoglobin Concentration in Sows and Neonatal Piglets." Proceedings of the Joint Meeting of the 5th European Symposium of Porcine Health Management and the 50th Anniversary Meeting of the Pig Veterinary Society of Great Britain, Edinburgh, United Kingdom (2013).
Leuillet, M. and E. Salmon-Legagneur. "Sur l'utilisation d'un composé de fer dextrane hydrogéné([1]) par injection chez la truie en gestation et en lactation." *Ann. Zootech.* 17.1 (1968): 59-70.
Moore, R.W. et al. "Iron Deficiency Anemia as a Cause of Stillbirths in Swine." *Journal of the American Veterinary Medical Association* 147.7 (1965): 746-748.
Morris, Christopher J. et al. "Reactive Oxygen Species and Iron—a Dangerous Partnership in Inflammation." *International Journal of Biochemistry and Cell Biology* 27.2 (1995): 109-122.

(Continued)

*Primary Examiner* — Ganapathy Krishnan
(74) *Attorney, Agent, or Firm* — Robin L. Teskin; Baker, Donelson, Bearman, Caldwell & Berkowitz PC

(57) ABSTRACT

The present invention relates to an iron carbohydrate complex for use in a method of increasing the blood haemoglobin concentration in a pregnant non-human mammal, wherein the pregnant non-human mammal having a blood haemoglobin level of 105 g/L or less, is administered one or more doses of iron carbohydrate complex comprising an amount of elemental iron of 1800 mg or more per dose. The method relates to the further effects of decreasing the rate of stillborn offsprings from a pregnant non-human mammal having a blood haemoglobin level of 105 g/L or less, increasing the blood haemoglobin concentration of offspring litters within 3 days from birth and/or weaning, or increasing the litter size in a subsequent parity of a non-human mammal having a blood haemoglobin level of 105 g/L or less.

17 Claims, No Drawings

(56) References Cited

OTHER PUBLICATIONS

Randall, G.C.B. and R.H.C. Penny. "Stillbirths in Pigs: the Possible Role of Anoxia." *The Veterinary Record* 81 (1967): 359-361.
Rootwelt, et al. "Associations between intrapartum death and piglet, placental, and umbilical characteristics." *Journal of Animal Science* 90 (2012): 4289-4296.
Sakai, Takeo et al. "The Preventive Effect of Dietary Iron-D, L-Threonine Supplement on Anemia in Young Pigs." *Bulletin of the College of Agriculture and Veterinary Medicine, Nihon University* 43 (1986): 217-223.
Svetina, Ante, et al. "Relation between erythrocyte parameters and stillbirth in piglets." *Veterinarski Arhiv* 76.4 (2006): 297-303.
Thorn, Catherine E. "Chapter 109: Hematology of the Pig." *Schalm's Veterinary Hematology Sixth Edition*, Wiley-Blackwell, Ames, Iowa, Weiss, D, and Wardrop, K. eds. (2010): 843-851.
Vinther, Jens. "National Average for Productivity in Pork Production 2012." Videncenter for Svineprodktion (Pig Research Centre). Jun. 11, 2013.
Wei, K.Q. et al. "Effects of Iron from an Amino Acid Complex on the Iron Status of Neonatal and Suckling Piglets." *Asian Australian Journal of Animal Science* 18.10 (2005): 1485-1491.
Zaleski, Halina M. and Roger R. Hacker. "Variables related to the progress of parturition and probability of stillbirth in swine." *The Canadian Veterinary Journal* 34 (1993): 109-113.
Ducsay CA, et al. "Role of uteroferrin in placental iron transport: effect of maternal iron treatment on fetal iron and uteroferrin content and neonatal hemoglobin," J Anim Sci. Nov. 1984;59(5):1303-8. (9 pages).
Jensen, AK., Nielsen, J.P., 2014. Association between stillborn piglets and haemoglobin concentration in sows at farrowing. In Proceedings of the 6th ESPHM, Sorrento, Italy, p. 127 (2 pages).
Pollmann DS, et al. "Comparison of gleptoferron with iron dextran for anemia prevention in young pigs," Conference: Swine Day, Manhattan, KS, Nov. 11, 1982, pp. 46-50. (5 pages).
Rydberg et al., "The Effect of Pre-Partum Intramuscular Iron Treatment of Dams on Litter Hemoglobin Levels," Journal of Animal Science 1959, vol. 18, No. 1, pp. 415-419. (5 pages).
Beliles et al. "The effect of massive transplacental iron loading." Toxicology. Nov. 1, 1975;5(2):147-58.

\* cited by examiner

TREATMENT OR PREVENTION OF ANAEMIA IN PREGNANT NON-HUMAN MAMMALS

CROSS-REFERENCE TO RELATED APPLICATIONS

This application is a national phase under 35 U.S.C. § 371 of PCT International Application No. PCT/DK2015/050328 which has an International filing date of Oct. 27, 2017, which claims priority to Danish Patent Application No. PA 2014 70654, filed Oct. 27, 2014, the entire contents of each of which are hereby incorporated by reference.

FIELD OF THE INVENTION

The present invention relates to the treatment of anaemia in pregnant non-human mammals with iron carbohydrate complexes. The invention generally improves the haemoglobin level of the non-human mammal and/or parameters, which are measured on offspring, such as the stillborn rate, the mortality rate in the suckling period, the increase in the haemoglobin level, and the growth rate in the suckling period.

PRIOR ART

Several studies suggest that anaemia is highly prevalent in sows although rarely diagnosed in veterinary practice. A recent Danish investigation demonstrated that 59% of sows in a large commercial Danish herd had blood haemoglobin (Hb) concentrations below 110 g/l (Jensen et al, 2014), which is considered as a lower limit reference value for pregnant sows (Thorn, 2010).

The most common reason for anaemia is iron deficiency. As iron is involved in the transport of oxygen, in the synthesis of DNA and in many other processes maintaining normal structure and function of cells (Morris et al., 1995), a low iron status will have several visible and invisible effects on health and production of the sows and their offspring litters.

Recently it was shown that high sow haemoglobin levels during pregnancy are associated with reduced rate of stillborn piglets (Jensen et al 2014). The relation between haemoglobin level in sows and the rate of stillbirth has been studied earlier in sows that were less prolific than the present breeds (Archibald and Hancock, 1939, Moore et al., 1965, Zaleski and Hacker, 1993).

It has also been shown that the stillborn piglets have lower haemoglobin values than live born piglets (Svetina et al., 2006; Zaleski and Hacker, 1993) and that 75% of the stillborn piglets die during delivery (Glastonbury, 1977; Leenhouwers et al., 1999). Furthermore, the haemoglobin level in the sow is associated with the haemoglobin level of the offspring piglets (Jensen and Nielsen, 2013). The most obvious explanation for the observed effect of high haemoglobin levels on the stillbirth rate is the reduced risk of hypoxia in sows and piglets and increased vigour of the piglets during parturition. Therefore, improvement of haemoglobin levels in sows may open effective means for reduction of stillbirths.

In Denmark stillbirth losses average 1.7 piglets per litter (Vinther, 2013) and thereby impose a serious economic and welfare issue in pig production. Herd interventions in order to reduce number of stillbirths are often difficult to apply and can only rarely be contributed to infectious or management factors.

It is a standard procedure to iron supplement piglets in the suckling period and the industrial standard is injection of 200 mg elemental iron during the first days of life. Until the resulting haemoglobin production is achieved the piglet is solely depending on the iron obtained during pregnancy from placenta in utero from the sow.

Attempts to increase the level of haemoglobin in sows by injecting Gleptosil in an amount of 2 g 7 weeks and 4 weeks prior to the expected farrowing was not successful (Auvigne, 2009). For sows having between 107.7 to 117.3 g/L haemoglobin in the blood, the parenteral administering of an iron carbohydrate did not result in an increase in the blood haemoglobin concentration.

Piglets born with high haemoglobin levels have an increased chance of survival until weaning, and it is an aim of the present invention to provide an iron supplementation for pregnant sows that can increase the haemoglobin levels of the sows and/or improve parameters measured on offspring litters.

DISCLOSURE OF THE INVENTION

The present invention relates to an iron carbohydrate complex for use in a method of increasing the blood haemoglobin concentration in a pregnant non-human mammal, wherein the pregnant non-human mammal having a blood haemoglobin level of 105 g/L or less, is administered one or more doses of iron carbohydrate complex comprising an amount of elemental iron of 1800 mg or more per dose.

In another aspect the invention relates to an iron carbohydrate complex for use in a method of decreasing the rate of stillborn offspring from a pregnant non-human mammal, wherein the pregnant non-human mammal having a blood haemoglobin level of 105 g/L or less is administered one or more doses of iron carbohydrate complex comprising an amount of elemental iron of 1800 mg or more per dose.

In yet another aspect the invention relates to an iron carbohydrate complex for use in a method of increasing the blood haemoglobin concentration of offspring litters within 3 days from birth and/or at weaning, wherein a pregnant non-human mammal having a blood haemoglobin level of 105 g/L or less is administered one or more doses of iron carbohydrate complex comprising an amount of elemental iron of 1800 mg or more per dose.

In yet another aspect the invention relates to an iron carbohydrate complex for use in a method of increasing the litter size in a subsequent parity of a non-human mammal, wherein the pregnant non-human mammal having a blood haemoglobin level of 105 g/L or less is administered one or more doses of iron carbohydrate complex comprising an amount of elemental iron of 1800 mg or more per dose.

Iron deficiency anaemia during pregnancy is understood to be a common problem for most mammals due to loss increase in blood volume and changes in metabolism associated with fetus growth. It has been studied in detail and is commonly treated in humans. In non-human mammals, iron deficiency anemia is best understood in pigs, with most work focusing on iron deficiency anemia in piglets on an all-milk diet, where the condition is endemic. Unlike most other non-human mammals, iron deficiency anemia and its treatment has also been studied in the pregnant sow and thus the present invention is based on sows as the exemplary of pregnant non-human mammals. While the present invention herein mostly is described using pigs as an exemplary non-human mammal, it will be evident for the person skilled in the art that the invention can be performed on any non-human mammal. In a certain aspect of the invention the non-human mammal is a pig, a horse, camel, sheep, goat, or a cow.

An early warning of the blood haemoglobin level decreasing to 105 g/L or less is a decreased level of ferritin concentration since the ferritin level expresses the iron storage of the organism. The present invention therefore also covers prophylactic treatment of a pregnant non-human mammal having a low ferritin level that predicts the decreasing of the blood haemoglobin level to 105 g/L or less if the pregnant non-human mammal is not treated in accordance with method of the present invention.

A dose in the context of the present invention may be a single administering or two or more administrations performed on the same day. Alternatively, two or more administrations may be administered to the non-human mammal within a time period of 5 days or less, such as 4, 3, or 2 days. Each administration may be given either through an enteral or a parenteral route. In a preferred aspect of the invention the dose is parenterally administered. A preferred parental administering is by injection or infusion. In a certain embodiment two injections or infusions are administered to each side of the non-human mammal's neck on the same day.

According to the present invention, the non-human mammal is administered one or more doses, such as two, three, four, five, six or more doses during pregnancy. In addition, when two or more doses are administered, the distance in time between each dose is 1 week or more, such as 2 weeks, 3 weeks, 4 weeks, 5 weeks, 6 weeks, or more. When two doses are administered, the first dose being administered 15 to 3 weeks prior to expected farrowing and the second dose being administered 8 to 1 weeks prior to expected farrowing.

The iron carbohydrate complex of the invention is believed to increase the blood haemoglobin in an anaemic non-human mammal, such as a sow. This in itself is important since it improves the health and general well-being of the sow. Moreover, in certain embodiments, the present inventors have now found that administration of the iron carbohydrate complex of the invention to an anaemic, pregnant sow also have an effect on the offspring of the sow. Thus, when the iron carbohydrate complex is administered to the pregnant anaemic sow, one or more times prior to farrowing of the sow, the administration will also increase the blood haemoglobin level of the offspring piglets.

As a first effect the administration to the mother sow will decrease the rate of stillborn piglets. By stillborn is meant that the lungs are inflated. In another embodiment, the rate of mummified piglets is decreased. A mummified piglet is defined as a piglet in which the lungs are not inflated. Thus, a higher percentage of the litter will be live born. When the term litter size is used it is be understood as the total size or number of still born and live born piglets. Further, the administration to the mother sow may increase the blood haemoglobin concentration, survival, health and/or growth of offspring litters until weaning. In a preferred aspect of the invention, the average rate of stillborn offsprings is 12% or less, such as 11%, 10%, 9%, 8%, 7%, 6%, 5%, 4%, 3%, 2%, 1% or less. In another aspect of the invention, average survival rate until weaning is 80% or more such as 81%, 82%, 83%, 84%, 85%, 86%, 87%, 88%, 89%, 90%, 91%, 92%, 93%, 94%, 95%, 96%, 96%, 97%, 98%, 99% or more. The average survival rate is calculated on the basis of live born piglets, i.e. total number of piglets subtracted still born or mummified piglets, and the piglets alive at weaning.

Thus, from farrowing until weaning more offspring from a litter will survive compared to a situation where the iron carbohydrate complex is not administered to the pregnant, anaemic sow. Moreover, the offspring will be in better health at weaning, e.g. expressed with health parameters, such as increased gain in weight or a higher blood haemoglobin concentration. When the iron carbohydrate complex is administered to the pregnant, anaemic sow the offspring will have gained more weight and/or a higher blood haemoglobin concentration until weaning than if the iron carbohydrate complex was not administered to the pregnant, anaemic sow. In a certain embodiment, the present inventors have observed that when the iron carbohydrate complex is administered to the pregnant, anaemic sow according to the invention, there is a reduced need to administer additional iron, enterally or parenterally, to the piglets, in the suckling period. Thus, the invention simplifies the tasks of the pig farmer and improves the general well being of both the mother sow and the offspring.

By the treatment of the present invention the average litter size may be increased in a subsequent parity, to a level where the average litters size is 13 or more, such as 14, 15, 16, 17, or more. In addition, the average haemoglobin concentration in a pregnant sow is increased by 1% or more, such as 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50% or more. Furthermore, in a preferred aspect of the present invention, the average rate of stillborn offsprings is decrease by 1% or more, such as 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50% or more. In a certain embodiment of the invention, the average blood haemoglobin concentration of offspring litters until weaning is increased by 1% or more, such as 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50% or more. In an aspect of the invention, the average litter size of a pregnant sow in a subsequent parity is increased by 1% or more, such as 2%, 3%, 4%, 5%, 6%, 7%, 8%, 9%, 10%, 11%, 12%, 13%, 14%, 15%, 16%, 17%, 18%, 19%, 20%, 25%, 30%, 40%, 50% or more.

The sow treated according to the present invention may be in a variety of health conditions as reflected by the back fat thickness. In a preferred aspect, the sow has a back fat thickness of 17 mm, 16 mm, 15 mm, 14 mm, 13 mm, 12 mm, 11 mm, 10 mm, or less. Likewise, the sow may have had one or several parities; preferably, for the sow treated the parity of the sow is 2, 3, 4, 5, 6, 7, 8, 9, or more.

In the context of the invention the iron carbohydrate complex is any complex of iron ions or iron particles comprising $Fe^{3+}$ and/or $Fe^{2+}$ and a carbohydrate, suitable for administering to pigs. In a certain aspect of the invention it is preferred that the iron carbohydrate complex can penetrate placenta of the sow, thereby entering the foetus. Iron carbohydrate complexes are well-known to the skilled person and the specific selection of a suitable iron carbohydrate complex is within the knowledge of the skilled person. In a preferred embodiment the iron carbohydrate complex is formulated as an injectable veterinary composition, having a content of elemental iron in the interval of 5-25% (w/v), e.g. 50-250 g/L, complexed with the carbohydrate. The veterinary composition may comprise auxiliaries usually applied in this field. Moreover, the veterinary composition comprising iron carbohydrate complex may or may not contain a preservative, such as phenol in an amount of 1-10 g/L. In a certain embodiment the amount of phenol is less than 1 g/L. If needed, sterilisation is obtained in an alternative way.

The iron carbohydrate complex may be selected from a variety of different substances. Preferably, the iron carbohydrate complex is selected from the group comprising iron carboxymaltose, iron polyglucose sorbitol carboxymethyl ether complex, iron mannitol complex, iron dextran, iron hydrogenated dextran, carboxyalkylated reduced oligo- and poly saccharides, iron sucrose, iron gluconate, iron dextrin, iron hydrogenated dextrin, iron polymaltose, iron hydrogenated polymaltose, iron polyisomaltose, iron hydrogenated polyisomaltose, iron saccharide complex, iron pyrophosphate, iron sorbitol, glycoheptanoic acid, oxidised dextran, oxidised dextran, oxidised oligo and poly-saccharides or mixtures thereof. In a certain embodiment the iron is complexed with dextran glucoheptonic acid. This iron carbohydrate complex is also known as Gleptoferron and is obtainable as eg. Gleptosil (Alstoe Limited Animal Health, York, GB), Ursoferran (Serumwerk Bernburg AG, Bernburg, D). In another embodiment, the iron is complexed to hydrogenated dextran. Commercial iron hydrogenated dextran complexes are Uniferon, CosmoFer, MonoFer, and DiaFer obtainable from Pharmacosmos A/S, Holbaek, Denmark.

The carbohydrate component of the iron carbohydrate complex of the present invention may have any suitable molecular weight. It is generally preferred to use a carbohydrate component with a molecular weight in which weight average molecular weight (MW) of the carbohydrate component of the iron carbohydrate complex is 800 to 80,000 Dalton, preferably 800 to 10,000 Dalton. A weight average molecular weight in this range may easier be conveyed from the pregnant sow to the foetus. In a preferred aspect, the apparent molecular weight of the iron carbohydrate complex is 500.000 Dalton or less, such as an apparent molecular weight of 400.000 Dalton or less.

The dose of the iron carbohydrate complex is generally calculated on the basis of elemental iron and is generally in the range of 1800 mg to 10.000 mg. In a certain embodiment the dose is 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg 4100 mg, 4200 mg, 4300 mg, 4400 mg, 4500 mg, 4600 mg, 4700 mg, 4800 mg, 4900 mg, 5000 mg, 5100 mg, 5200 mg, 5300 mg, 5400 mg, 5500 mg, 5600 mg, 5700 mg, 5800 mg, 5900 mg, 6000 mg, 6100 mg, 6200 mg, 6300 mg, 6400 mg, 6500 mg, 6600 mg, 6700 mg, 6800 mg, 6900 mg, 7000 mg, 7100 mg, 7200 mg, 7300 mg, 7400 mg, 7500 mg, 7600 mg, 7700 mg, 7800 mg, 7900 mg, 8000 mg, 8100 mg, 8200 mg, 8300 mg, 8400 mg, 8500 mg, 8600 mg, 8700 mg, 8800 mg, 8900 mg, 9000 mg, 9100 mg, 9200 mg, 9300 mg, 9400 mg, 9500 mg, 9600 mg, 9700 mg, 9800 mg, 9900 mg, 10000 mg, or more. In certain circumstances it may be suitable to administer a dose of 1650 mg, such as 1700 mg, such as 1750 mg or more elemental iron.

A dose in this range will be applicable to a sow of a typical size, e.g. with a body weight (BW) of about 250 kg. Since the weight of the sow varies with race and nutrition, the dose may in some embodiments better be expressed based on the body weight of the sow. Thus, the dose of iron, i.e. elemental iron, may be in the range of 6 mg/kg BW to 30 mg/kg BW, such as 7 mg/kg BW, 8 mg/kg BW, 9 mg/kg BW, 10 mg/kg BW, 11 mg/kg BW, 12 mg/kg BW, 13 mg/kg BW, 14 mg/kg BW, 15 mg/kg BW, 16 mg/kg BW, 17 mg/kg BW, 18 mg/kg BW, 19 mg/kg BW, 20 mg/kg BW, 21 mg/kg BW, 22 mg/kg BW, 23 mg/kg BW, 24 mg/kg BW, 25 mg/kg BW, 26 mg/kg BW, 27 mg/kg BW, 28 mg/kg BW, 29 mg/kg BW, 30 mg/kg BW, or more.

The iron carbohydrate complexes of the present invention are suited for use in methods where the iron carbohydrate complex is injected into a sow having a blood haemoglobin level of 105 g/L or less. However, it is contemplated that the iron carbohydrate complex will have the desired effect on all sows irrespective of the blood haemoglobin level. Thus, it is contemplated that the iron carbohydrate complex may also be effective if the sow has a blood haemoglobin level of about 110 g/L or less, such as 109 g/L, 108 g/L, 107 g/L, 106 g/L or less. In general the treated sow has a blood haemoglobin level of 105 g/L or less, such as 104 g/L, 103 g/L, 102 g/L, 101 g/L, 100 g/L, 95 g/L, 90 g/L, 85 g/L, 80 g/L, 75 g/L, 70 g/L, 65 g/L, 60 g/L, 55 g/L, 50 g/L, 45 g/L, 40 g/l or less. Sows with blood haemoglobin at these levels may generally be referred to as "anaemic".

The sow to be treated with the iron carbohydrate complex is typically of second parity or higher. It is generally recognised that the blood haemoglobin level of a sow will decrease with increasing parity (Normand et al., 2012) and the present inventors have surprisingly found that the iron carbohydrate complex of the invention is especially effective when administered to sows of second or higher parity, such as third parity, fourth parity, fifth parity, sixth parity, seventh parity, eight parity ninth parity or higher. However, it is contemplated that the iron carbohydrate complex will also be effective if administered to an anaemic sow of first parity.

In a preferred aspect of the invention, the iron carbohydrate complex of the invention is for parental administration by injection, e.g. intramuscular (IM), subcutaneous (SC), or intravenous (IV) injection. IM injection is preferred, optionally as a bolus injection. The expected time of farrowing is well-known to the skilled person and may be calculated from the date of insemination or conception. Determination of the timing of the administration is thus calculated from the insemination or conception date.

To obtain the best effect on the piglets, it is generally believed that the last dose administering should be performed at the latest 1 week, preferably 2-4 weeks prior to farrowing. Within the last 20 days of pregnancy the foetus is expected to double its weight. The first dose should generally be delivered 15 weeks prior to farrowing. However, the above indications are just guiding and iron carbohydrate complex administered outside the preferred period of 15 weeks to 2 weeks prior to farrowing may provide a valuable effect.

The dose of iron carbohydrate complex is administered to the pregnant, anaemic sow at one or more points of time, such as two, three, four, five, six or more doses during pregnancy, and preferably within the period of 15 weeks to 2 weeks prior to farrowing of the sow. Thus, at each administration 1,800 mg to 10,000 mg elemental iron formulated as the iron carbohydrate complex is administered, e.g. IM, SC or IV, to the pregnant, anaemic sow. The dose at each administering may be the same or the doses may be different. For example, the first injection may be larger than the second injection, such as 500 mg, 1000 mg, 1500 mg, 2000 mg larger, or vice versa. Usually, it is sufficient to administer two doses within the period from 9 weeks to 3 weeks prior to farrowing. The distance in time between each dose may be 1 week or more, such as 2 weeks, 3 weeks, 4 weeks, 5 weeks, 6 weeks or more.

The iron carbohydrate complex can be administered together with other veterinary medicaments. Examples of another veterinary medicament type include vaccines, such as the PRRS vaccine. Also antibiotics may be administered together with the iron carbohydrate complex. Examples of antibiotics include amikacin, aminopenicillins, amoxicillin, azithromycin, ceohalospirins, ciprofloxacin, clinamycin, doxycycline, enrofloxacin, erythromycin, penicillin, gentamicin, kanamycin, lincomycin, marbofloxacin, metronidazole, novobiocin, orbifloxacin, penicillin G, penicillininase-resistant penicillins, sulfadimethoxine, tetracycline, thiabendazole, neomycin, dexamethasone, trimethoprim, and tylosin. In a certain aspect the iron carbohydrat complex is administered together with erythropoietine to stimulate the production of blood cells.

The total amount of iron carbohydrate complex calculated as elemental iron is at least 1,800 mg or more elemental iron. In a preferred embodiment the total amount of elemental iron is 2,000 mg, 2,500 mg, 3,000 mg, 3,500 mg, 4,000 mg, 4,500 mg, 5,000 mg, 6,000 mg, 7,000 mg, 8,000 mg, 9,000 mg, 10,000 mg elemental iron or more. It is also contemplated that the total amount of iron, may be divided into a plurality of administrations in which some may contain less than 1800 mg/L.

DETAILED DESCRIPTION OF THE INVENTION

The present invention relates to an iron carbohydrate complex for use in a method of increasing the blood haemoglobin concentration, for use in a method of decreasing the rate of stillborn piglets, for use in a method of increasing the survival, health and/or growth of offspring litters until weaning, or for use in a method of increasing the litter size.

The following describes the experimental protocol supporting the invention.

1 Materials and Methods 1.1 Target and Study Population

The study is carried out in a commercial sow herd, which is representative of intensive sow herds in Denmark. The study population consists of pregnant sows with low haemoglobin values and their offspring litters until weaning. The pregnant sows are selected for the study between 60-80 days of gestation.

1.2 Study Design

The study is a randomised clinical trial. Approval from the Danish Animal Experiments Inspectorate and from The Danish Medical Agency is obtained before the start of the study. The study is carried out according to the protocol.

1.3 Study Unit

The study unit is sows and their offspring litters.

1.4 Herd Selection

A prevalence study of anaemia in Danish sows is carried out in 5 herds selected in cooperation with specialised veterinary pig practices. A herd with high prevalence of anaemia is selected for the study.

1.4.1 Herd Selection Criteria

1. Herd size of at least 1000 sows
2. Good record keeping of herd data
3. Motivated herd owner
4. Iron supplementation of piglets by injection of 200 mg iron dextran at day 4 only 1.4.2 Herd Exclusion Criteria 1. Provision of extra iron to the sows either orally or injectably (except in feed formulations)
2. Breeding or multiplying herd
3. Parturition induction e.g. with prostaglandin
4. Obvious infectious disease or management problems that may affect stillbirths 1.5 Sample Size The sample size necessary to estimate a prevalence is calculated by the equation:

$$N=(Z_{(1-\alpha/2)}^2 \sigma^2)/L^2 \text{ (J.P.T.M et al., 2001)}$$

N=the number of samples taken
$\alpha=0.05$ (95% level of confidence)$=>Z_{(1-0.05/2)}=Z_{0.975}=1.96$
=standard deviation
L=Expected Absolute Error In a herd with 50% of sows suffering from anaemia (<100 g Hb per litre) a sample size of 50 animals is sufficient to determine the prevalence with an allowable error of +/−13%.

1.6 Identification of Sows for Clinical Trial

All multiparous sows from a sufficient number of weekly batches corresponding to 200 animals will be identified at day 60-80 day of gestation. First parity sows will be excluded.

Initial measurement of haemoglobin in the 200 sows will be performed by HaemoCue measurement. Healthy sows with haemoglobin lower than 100 g/l will be included in the study.

1.7 Blood Sampling

The sows are restrained and 5 mL blood is sampled in EDTA and plain vacutainer tubes from the jugular vein at the start of the trial (week eleven of gestation) and one week before expected farrowing. The samples will be analysed by complete haematology, serum iron, TIBC and serum ferritin as described in sections 4.6.3 and 4.8. Transferrin saturation will also be calculated as described in section 4.9.

1.8 Haematology of Sows

All 200 EDTA stabilized blood samples will be tested initially for haemoglobin concentration by HaemoCue. The equipment necessary for this testing will be provided by Pharmacosmos. Selection of 100 anaemic sows will be based on this testing.

Samples from the 100 selected sows will subjected to complete haematology (baseline measurement) at the University of Copenhagen.

The blood samples are analysed for erythrocyte count (RBC), leucocyte count (total leucocyte count and differential leucocyte count), platelets, mean platelet volume (MPV), red blood cell distribution width (RDW), haemoglobin concentration (Hb), haemoglobin distribution width (HDW), haematocrit (HCT), mean cell volume (MCV), mean corpuscular haemoglobin (MCH) and mean cell haemoglobin concentration (MCHC). Reticulocyte indices will also be analysed, which include reticulocyte count (absolute and relative), reticulocyte haemoglobin content (Chr), mean reticulocyte corpuscular haemoglobin concentration (CHCMr), reticulocyte cellular volume (MCVr), reticulocyte red cell distribution width (RDWr) and reticulocyte haemoglobin distribution width (HDWr).

The serum samples are stored until study sows for clinical trial are identified.

1.9 Recording of Sow Data

For each sow the following recordings are made: Age of sow, age of first insemination, number of dead born and live born piglets in previous parity, date of insemination, date of farrowing and parity of the sow.

2 Sample Size Calculation for Clinical Trial

The sample size in each group necessary to calculate differences between groups of animals is calculated by the equation (Graat et al., 2001)

$$N=2\times(Z_\alpha+Z_\beta)^2 * SD^2/\Delta^2$$

In which
N=Number of sows required in each group
$Z_\alpha$, $Z_\beta$=Values of Standard Normal distribution at specified levels of confidence and power
SD=Standard deviation
$\Delta$=Estimated difference The constant 2 implies that the SD is equal in both groups.

We assume a two sided test with α of 0.05, Z 0.05=1.96 and a power of 80%, $Z_{0.20}$=0.84.

The haemoglobin difference between two groups (Δ) is assumed to be 10 g/L and the SD is set to 15 g/L based on previous study.

When assuming a haemoglobin concentration difference of 9 g/L between treatment and control groups, 50 sows are required per group.

2.1 Laboratory Analysis of Frozen Samples

Serum samples obtained from the selected 100 sows (50 in treatment and 50 in control groups) are analysed for serum iron, total iron binding capacity (TIBC) and serum ferritin, if possible. Serum iron and total iron binding capacity are analysed at the Central Laboratory, University of Copenhagen whereas serum ferritin measurement is performed at professor Ritzmanns laboratory, Tierärztliche Fakultät, Ludwig-Maximilians-Universität, München.

2.2 Calculation of Transferrin Saturation (TfS)

Transferrin saturation is calculated for all the blood samples using the formula: TfS (%)=Serum iron/TIBC×100.

2.3 Measurement of Back Fat Thickness

Baseline back fat measurement of the sows is done using ultrasonic device. The measurement is taken at the last floating rib, 7 cm on either side of the midline of the back according to the guidelines of the manufacturer. Back fat measurement will be performed at start of the trial, at farrowing and at immediately before weaning.

2.4 Randomization of Sows

The selected sows are randomly allocated to two groups:
1. Control group
2. Treatment group Randomisation is done using lottery with ear tag numbers of sows.

2.5 Treatment of Sows

Preparations of test and control substance and equipment for injection will be provided by Pharmacosmos.

First Dose

Sows in the treatment group will receive 12.5 mL (2,500 mg) iron injection (Uniferon) intramuscularly in the neck region at day 70 of gestation (6 weeks before farrowing). The control group will receive 12.5 mL of isotonic saline intramuscularly in the neck region in the same day. Any reactions due to the iron injection are noted and treated accordingly.

Second Dose

Two weeks after the first dose of iron at day 84 (4 weeks before farrowing), the sows will receive second dose of 12.5 mL (2,500 mg) iron injection (Uniferon) intramuscularly in the neck region intramuscularly. Also, the control sows will receive second dose of isotonic saline.

2.6 Management of Sows of Piglets

All sows are managed according to standard procedures at the farm during the entire study period.

2.7 Recording and Classification of Stillborn Piglets

All fully developed dead piglets in a litter are collected at farrowing. The dead piglets are necropsied and lungs are tested. If the lungs sink in water, the piglet is considered as stillborn. Stillborn piglets are classified as follows:

1. Non-fresh stillbirths: Showing signs of degeneration, brown skin colour—these piglets probably die more than a week before onset of farrowing (Randall and Penny 1967)

2. Pre-partum stillbirths: Showing no external signs of decay but with the same brick-red colour of all their abdominal organs due to haemolysis and autolysis—these pigs die in utero in the days closely preceding farrowing (Bille et al., 1974)

3. Intra-partum stillbirths: Normal colour of the abdominal organs but presence of mucus and/or meconium in the trachea indicating piglets dying during farrowing Mummified foetus is recorded but not included in the trial. For each stillborn and live born piglets, the sex is recorded and individual bodyweight obtained, if practically feasible.

2.8 Haematology of Piglets

Blood is collected from the Anterior Vena cava from a subset of two live born piglets per litter. These piglets are selected randomly among all the piglets in that particular litter. The blood from two dead born piglets per litter is collected according to the guidelines of Rootwelt et al., 2012.

The blood is subjected to complete haematology including serum iron, TIBC and serum ferritin as described in sections 1.8 and 2.1. Lactate in each piglet will also be measured.

2.9 Adverse Reactions in Sows

During the study it is expected that 20% of sows are culled at weaning. Among these sows 10 animals are selected by convenience for studies on injection site reactions. The injection site is assessed macroscopically to determine the extent of tissue damage caused due to injection. Samples for histological examination will be fixed in formalin.

The number of total born piglets in treated animals will be compared to those of controls. The back fat thickness of sows close to weaning will be recorded.

3 Statistical Analyses

SAS 9.3 is employed for the data analysis. The haematology of sows before and after iron injection are compared using general linear model using PROC GLM procedure in SAS. The differences in haematology in sows between control and treatment sows are calculated using general linear model with PROC GLM procedure. Explanatory factors will include baseline Hb values, number of total born piglets and parity of the sow. The probability of piglet being stillborn in each control and treatment sows is calculated using generalised linear models using PROC LOGISTIC procedure. In this procedure, Hb at baseline measurement, number of total born piglets, parity of the sow, sex of the piglet are explanatory variables that are considered for analysis.

The differences in haematology between live and stillborn piglets are carried out using linear mixed model with PROC MIXED procedure with sow as the random factor. Other explanatory variables will include litter size, parity of the sow and haemoglobin of the sow.

Example 1

100 sows were selected from a herd showing a high prevalence of anaemia. For practical reasons the study was performed in two batches. All data was pooled.

5 ml blood was sampled in EDTA from the jugular vein at the start of the trial, i.e. week 8 of gestation, about one week before expected farrowing, and 4 week after farrowing. The blood samples were marked Hb_S1, Hb_S2, and Hb_S3, respectively. The samples were analysed and the blood haemoglobin concentration (Hb) was determined.

The selected sows are randomly allocated to two groups:
1. Control group (C)
2. Treatment group (T)

Randomisation is done using lottery with ear tag numbers of sows. Each group included 50 sows.

Sows in the treatment group was delivered a first dose of 12.5 ml iron dextran (Uniferon, 20%), corresponding to 2500 mg iron, intramuscularly in the neck region at day 70 of gestation (6 weeks before farrowing). The control group received 12.5 mL of isotonic saline intramuscularly in the neck region in the same day. Any reactions due to the iron injection are noted and treated accordingly.

Two weeks after the first dose of iron at day 84 (4 weeks before farrowing), the sows received a second dose of 12.5 mL (2,500 mg) iron injection (Uniferon) intramuscularly in the neck region. Also, the control sows will received second dose of isotonic saline.

TABLE 1

Hb in Sows

| Baseline Hb (g/l) | Group | Number of sows | Average Hb_S1 | Average Hb_S2 | Average Hb_S3 | Δ (Hb_S1, Hb_S2) | Δ (Hb_S1, Hb_S3) |
|---|---|---|---|---|---|---|---|
| <105 | C | 29 | 99.33 | 99.60 | 99.55 | 0.28 | 0.22 |
|  | T | 31 | 99.10 | 100.51 | 100.77 | 1.40 | 1.66 |
| >105 | C | 19 | 111.16 | 103.36 | 103.19 | −7.80 | −7.97 |
|  | T | 19 | 111.07 | 102.26 | 101.66 | −8.82 | −9.41 |

All fully developed dead piglets in a litter are collected at farrowing. The dead piglets are necropsied and lungs are tested. If the lungs sink in water, the piglet is considered as stillborn.

Mummified foetus is recorded but not included in the trial. For each stillborn and live born piglet, the sex is recorded and individual bodyweight obtained, if practically feasible.

TABLE 2

Total of stillborn piglets

| Baseline Hb (g/l) | Group | Number of sows | Number stillborn | Sum of liveborn | Stillborn rate |
|---|---|---|---|---|---|
| <105 | C | 28 | 44 | 477 | 7.9% |
|  | T | 27 | 32 | 451 | 6.6% |
| >105 | C | 16 | 20 | 276 | 6.6% |
|  | T | 16 | 18 | 255 | 6.4% |

It is noted that the haemoglobin concentration in sows shown in table 1 is increased for the sows having a baseline Hb below 105 g/l. Specifically, the anaemic sows having a low baseline Hb of <105 g/l experience an increase of 1.40 g/l, compared to 0.28 g/l for the control group, from the start of the trial to one week before expected farrowing and an increase of 1.66 g/l, compared to 0.22 for the control group, from the start to 4 weeks after farrowing. The results show that anaemic pregnant sows benefit from the administration of the iron carbohydrate complex. The Δ(Hb_S1, Hb_S2) and Δ(Hb_S1, Hb_S3) for sows having baseline Hb above 105 g/l are negative indicating that these animals are not benefitting from the treatment.

The stillborn rate in table 2 is decreasing from 7.9% in the control group to 6.6% in the treated group, when the sows having a baseline <105 g/l are treated with the iron carbohydrate complex. The result indicates that the rate of stillborn offspring is decreased by the administration of an iron carbohydrate complex. Conversely, the stillborn rate is decreasing from 6.6% in the control group to 6.4% in the treated group when the baseline Hb is above 105 g/l, indicating that an improvement in the stillborn rate for this group of sows is not obtained.

REFERENCES

Archibald, R., Hancock, E. E. I., 1939. Iron Deficiency-Stillbirth of Swine. Canadian Journal of Comparative Medicine 3, 134.

Bille, N., Nielsen, N. C., Larsen, J. L., Svendsen, J., 1974. Preweaning mortality in pigs. 2. The perinatal period. Nordisk veterinaermedicin, 26, 294-313.

Graat, E. A. M., Frankena, K., Bos, H., 2001. Principles and methods of sampling in animal disease surveys, In: Noordhuizen, J. P. T. M., Frankena, K., Thrusfield, M. V., Graat, E. A. M. (Eds.) Application of quantitative methods in veterinary epidemiology. Wageningen Pers, Wageningen, The Netherlands, pp. 45-46.

Jensen, A. K., Pedersen, K. S., Nielsen, J. P., 2013. Association between blood haemoglobin concentration in sows and neonatal piglets. In Proceedings of the 5th ESPHM, Edinburgh, UK.

Jensen, A. K., Nielsen, J. P., 2014. Association between stillborn piglets and haemoglobin concentration in sows at farrowing. In Proceedings of the 6th ESPHM, Sorrento, Italy.

Moore, R., Redmond, H., Livingston Jr, C., 1965. Iron deficiency anemia as a cause of stillbirths in swine. Journal of the American Veterinary Medical Association 147, 746.

Morris, C. J., Earl, J. R., Trenam, C. W., Blake, D. R., 1995. Reactive oxygen species and iron—a dangerous partnership in inflammation. The international journal of biochemistry and cell biology 27, 109-122.

Randall, G. C. B., Penny, R. H. C., 1967. Still birth in pigs: the possible role of anoxia. Veterinary Record 81, 359-361.

Rootwelt, V., Reksen, O., Farstad, W., Framstad, T., 2012. Associations between intrapartum death and piglet, placental, and umbilical characteristics. Journal of Animal Science 90, 4289-4296.

Svetina, A., Vrabac, L., Belić, M., Turk, R., 2006. Relation between erythrocyte parameters and stillbirth in piglets. Veterinarski arhiv 76, 297-303.

Thorn, C. 2010. Hematology of the pig. In Schalm's Veterinary Hematology 6th Edition, Wiley-Blackwell, Ames, Iowa, Weiss, D., Wardrop, K., eds. (Iowa, Wiley-Blackwell), p. 848.

Vinther J., 2013. National average productivity in pig production in 2012 (Landsgennemsnit for productivitet i svineproduktionen 2012). Videncenter for svineproduktion Zaleski, H. M., Hacker, R. R., 1993. Variables related to the progress of parturition and probability of stillbirth in swine. The Canadian Veterinary Journal 34, 109.

Auvigne, V., et al., 2010. Anaemia in the hyperprolific sow: Effect of injectable iron administration and relation with fattering score.

The invention claimed is:

1. A method of increasing the blood haemoglobin concentration in a pregnant non-human mammal, wherein the pregnant non-human mammal having a blood haemoglobin level of 105 g/L or less is parenterally administered one or more doses of an iron carbohydrate complex in an amount of 1800 mg to 10000 mg elemental iron per dose.

2. A method of decreasing the rate of stillborn offspring from a pregnant non-human mammal, wherein the pregnant non-human mammal having a blood haemoglobin level of 105 g/L or less is parenterally administered one or more doses of an iron carbohydrate complex in an amount of 1800 mg to 10000 mg elemental iron per dose.

3. The method according to claim 1, wherein the non-human mammal is a pig, a horse, camel, sheep, goat, or a cow.

4. The method according to claim 1, wherein the mammal is a pig.

5. The method according to claim 1, wherein two doses are administered, the first dose being administered 15 to 3 weeks prior to expected farrowing and the second dose being administered 8 to 1 weeks prior to expected farrowing.

6. The method according to claim 1, wherein the dose of elemental iron is 6 mg/kg BW (body weight) or more, or 7 mg/kg BW, 8 mg/kg BW, 9 mg/kg BW, 10 mg/kg BW, 11 mg/kg BW, 12 mg/kg BW, 13 mg/kg BW, 14 mg/kg BW, 15 mg/kg BW, 16 mg/kg BW, 17 mg/kg BW, 18 mg/kg BW, 19 mg/kg BW, 20 mg/kg BW, 21 mg/kg BW, 22 mg/kg BW, 23 mg/kg BW, 24 mg/kg BW, 25 mg/kg BW, 26 mg/kg BW, 27 mg/kg BW, 28 mg/kg BW, 29 mg/kg BW, 30 mg/kg BW, 31 mg/kg BW, 32 mg/kg BW, 33 mg/kg BW, 34 mg/kg BW, 35 mg/kg BW, 36 mg/kg BW, 37 mg/kg BW, 38 mg/kg BW, 39 mg/kg BW, or 40 mg/kg BW.

7. The method according to claim 1, wherein in the iron carbohydrate complex comprises iron carboxymaltose, iron polyglucose sorbitol carboxymethyl ether complex, iron dextran, iron hydrogenated dextran, iron sucrose, iron gluconate, iron polymaltose, iron hydrogenated polymaltose, iron sorbitol, iron glycoheptanoic acid, or mixtures thereof.

8. The method according to claim 1, wherein the iron carbohydrate complex is iron hydrogenated dextran.

9. The method according to claim 1, wherein the weight average molecular weight of the carbohydrate component of the iron carbohydrate complex is 800 to 50,000 Dalton, or 800 to 10,000 Dalton.

10. The method according to claim 1, wherein the apparent molecular weight of the iron carbohydrate complex is 500.000 Dalton or less, or 400.000 Dalton or less.

11. The method according to claim 1, wherein the parenteral administration is selected among the group consisting of intramuscular (IM), subcutaneous (SC), and intravenous (IV) administering.

12. The method according to claim 1, wherein the amount of reprotoxic conservatives in the formulation comprising iron carbohydrate complex is 1 g/L or less.

13. The method according to claim 12, wherein the reprotoxic conservative is phenol.

14. The method according to claim 1, wherein the dose is administered in 2 minutes or less.

15. The method according to claim 1, wherein the iron carbohydrate complex is administered as a liquid veterinary composition, wherein the concentration of the iron carbohydrate complex in the liquid veterinary composition is in the range of 5 g/100 mL to 25 g/100 mL.

16. The method according to claim 2, wherein the non-human mammal is a pig, a horse, camel, sheep, goat, or a cow.

17. The method according to claim 2, wherein the non-human mammal is a pig.

* * * * *